(12) United States Patent
Goeke et al.

(10) Patent No.: US 8,933,231 B2
(45) Date of Patent: Jan. 13, 2015

(54) ORGANIC COMPOUNDS

(75) Inventors: Andreas Goeke, Winterthur (CH); Li Jun Zhou, Zhuji (CN)

(73) Assignee: Givaudan SA

( * ) Notice: Subject to any disclaimer, the term of this patent is extended or adjusted under 35 U.S.C. 154(b) by 54 days.

(21) Appl. No.: 13/699,448

(22) PCT Filed: Jun. 22, 2011

(86) PCT No.: PCT/EP2011/060451
§ 371 (c)(1),
(2), (4) Date: Nov. 21, 2012

(87) PCT Pub. No.: WO2011/161163
PCT Pub. Date: Dec. 29, 2011

(65) Prior Publication Data
US 2013/0129655 A1    May 23, 2013

(30) Foreign Application Priority Data

Jun. 22, 2010 (WO) ............... PCT/CN2010/000914

(51) Int. Cl.
| | | |
|---|---|---|
| *C11D 3/50* | (2006.01) | |
| *A23L 1/226* | (2006.01) | |
| *C07D 215/04* | (2006.01) | |
| *C07D 221/04* | (2006.01) | |
| *C11B 9/00* | (2006.01) | |
| *A61K 8/49* | (2006.01) | |
| *A61Q 5/00* | (2006.01) | |
| *A61Q 5/02* | (2006.01) | |
| *A61Q 13/00* | (2006.01) | |
| *A61Q 15/00* | (2006.01) | |

(52) U.S. Cl.
CPC ........... *A23L 1/22678* (2013.01); *C07D 215/04* (2013.01); *C07D 221/04* (2013.01); *C11B 9/0092* (2013.01); *A61K 8/4926* (2013.01); *A61Q 5/00* (2013.01); *A61Q 5/02* (2013.01); *A61Q 13/00* (2013.01); *A61Q 15/00* (2013.01); *C11D 3/50* (2013.01)
USPC ............................... 546/181; 512/10; 426/650

(58) Field of Classification Search
CPC .................................................... C07D 215/06

USPC ............................... 546/181; 512/10; 426/650
See application file for complete search history.

(56) References Cited

U.S. PATENT DOCUMENTS 3,954,794 A    5/1976   Plattier et al.

FOREIGN PATENT DOCUMENTS

| DE | 2437901 A1 | 6/1975 |
|---|---|---|
| WO | 2004048336 A1 | 6/2004 |

OTHER PUBLICATIONS

Kaufman, CA 63:10041, abstract only of J Het Chem, VOl2(1), pp. 91-92, 1965.*
Hoenel, CA 93:220557, abstract only of J Chem Soc, Perk Trans 1: Org and Bio-Org Chem, vol. 9, pp. 1933-1939, 1980.*
International Search Report for PCT/CN2010/000914 dated Mar. 31, 2011.
International Search Report for PCT/EP2011/060451 dated Sep. 30, 2011.
Written Opinion of the International Searching Authority for PCT/EP2011/060451 dated Sep. 30, 2011.
"Selectivity of Hydrogenations. Part 4: 6- and 8-Substituted Quinaldines, Yield of Tetrahydroderivatives and Basicities of Quinolines", by Michael Honel, et al., Monatshefte Fur Chemie, vol. 115, 1984, pp. 1219-1228, XP000002659285.

* cited by examiner

*Primary Examiner* — D M Seaman
(74) *Attorney, Agent, or Firm* — Norris McLaughlin & Marcus PA

(57) ABSTRACT

Compounds of formula (I)

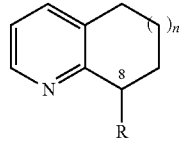

Formula (I)

wherein:
n=0, 1, 2, 3, and
R=C2-C6 linear and branched alkyl, alkenyl and cycloalkyl substituents are interesting flavor or fragrance ingredients having herbal-green aspects.

7 Claims, No Drawings

ORGANIC COMPOUNDS

This is an application filed under 35 USC 371 of PCT/EP2011/060451.

The present invention relates to fragrance and flavour ingredients that can deliver herbal-green odours.

Fragrance and flavour ingredients are known that are in the herbal-green family. Some examples of commercially available herbal-green ingredients include cis-3-hexenol, galbanum, pyrazines, perilla aldehyde and certain pyridines disclosed in WO2004048336.

Quinolines, however, would not be considered to be a class of molecule that would provide odourants or flavourants falling into the herbal-green family. For example, 2-isobutylquinoline has a minty, earthy, woody odour, whereas pyralone has an earthy, leathery woody, tobacco-like odour. Both of these materials are fully aromatic quinolines.

5,6,7,8-tetrahydroquinoline derivatives have been disclosed in the literature. Certain 5,6,7,8-tetrahydroquinoline derivatives have been disclosed in Monatshefte fuer Chemie 1984, 115, 1219; J. Chem. Soc. Perkin Tr. 1, 1980, 1933), however their odour descriptions were not depicted.

Other 5,6,7,8-tetrahydroquinoline derivatives have been disclosed (structures shown below), but likewise, in respect of each of these compounds, no odour description was reported.

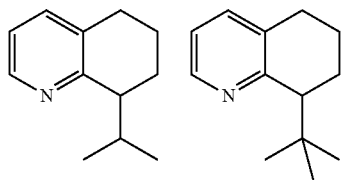

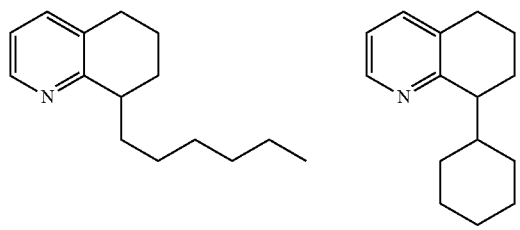

DE2437901, on the other hand, does describe the odour of a tri-substituted tetrahydroquinoline. More specifically this document describes 2,5-dimethyl-8-isopropyl-5,6,7,8-tetrahydroquinoline as having a distinctly spicy slightly amber-like odour, that is, quite unlike the characteristics of a herbal-green ingredient.

There remains a need to provide new flavour and fragrance ingredients that can be added to the palette of perfumers and flavourists alike, which impart herbal-green aspects to products to which they are applied.

Surprisingly applicant has found that certain 8-substituted 5,6,7,8-tetrahydroquinoline compounds agreeing with the formula (I) exhibit desirable herbal-green odours making them suitable for use in fragrance or flavour applications

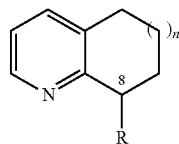

Formula (I)

wherein
n=0, 1, 2, 3 and
R=C2-C6 linear and branched alkyl, alkenyl and cycloalkyl substituents, provided very desirable odour profiles in the direction of fresh, green tomato leaf, ginseng and petitgrain odour, making these materials eminently suitable in applications in perfumery and flavours industry.

Applicant had investigated the hedonics of other substituted 5,6,7,8-tetrahydroquinoline compounds. Specifically, it was found that those materials substituted at the 8-position with a methyl group were found to have rather unpleasant chemical odours redolent of picoline, harsh minty notes that were not very desirable. Similarly, 8,8-disubstituted derivatives were found to be very weak odourants and undesirable for that reason. Furthermore, those materials substituted at the 2-position with a methyl group exhibited very weak and uninteresting odours.

Accordingly, in a first aspect of this present invention there is provided the use of compounds of formula (I) as flavour or fragrance ingredients.

As was discussed above, certain compounds falling within the formula (I) are known but their odours have never be described.

Accordingly, in yet another aspect of the present invention there is provided a compound of formula (I)

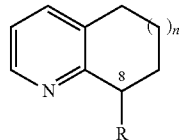

Formula (I)

wherein:
n=0, 1, 2, 3, and
R=C2-C6 linear and branched alkyl, alkenyl and cycloalkyl substituents
with the proviso that the compounds

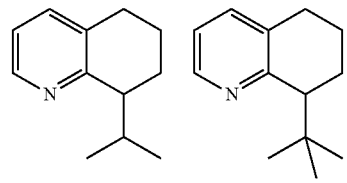

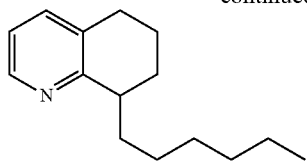
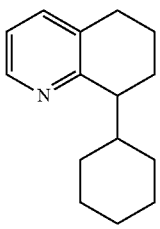

are excluded from the scope of the formula (I).

Preferred compounds of the formula (I) are:
8-sec-Butyl-5,6,7,8-tetrahydroquinoline
8-(Pentan-2-yl)-5,6,7,8-tetrahydroquinoline
8-(Pentan-3-yl)-5,6,7,8-tetrahydroquinoline
7-sec-Butyl-6,7-dihydro-5H-cyclopenta[b]pyridine
7-(Pentan-2-yl)-6,7-dihydro-5H-cyclopenta[b]pyridine
7-(Pentan-3-yl)-6,7-dihydro-5H-cyclopenta[b]pyridine
7-(3-Methylbut-2-enyl)-6,7-dihydro-5H-cyclopenta[b]pyridine The compounds of formula (I) can be prepared by alkylation of commercially available starting materials 5,6,7,8-tetrahydroquinoline, 6,7-dihydro-5H-cyclopenta[b]pyridines) or 6,7,8,9-tetrahydro-5H-cyclohepta[b]pyridine according to Scheme 1.

Scheme 1

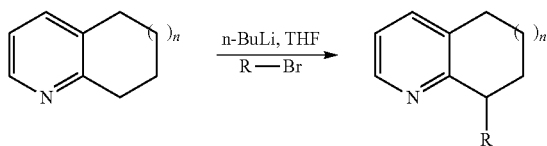

Further description of the synthetic route into specific compounds of the formula (I) is set out in the examples below.

Due to their desirable odour profiles, the compounds of formula (I) are suitable for use as fragrance ingredients in all manner of perfumery applications. Similarly, their odours may also add aroma to foodstuffs beverages and oral care products making them suitable as flavourant ingredients Accordingly, in another aspect of the invention there is provided a method to confer, enhance, improve or modify the hedonic properties of a perfuming composition or of a perfumed article, or of a flavour composition or flavoured article, which method comprises adding to said composition or article a compound of formula (I).

Due to the surprising properties of the compounds of formula (I), the present invention provides in another of its aspects a fragrance or flavour composition or a flavoured or perfumed article comprising a compound of formula (I).

Said fragrance or flavour composition may also comprise carrier materials for the compounds of the formula (I); a perfumery or flavour base; and other adjuvants useful in fragrance and flavour formulations.

The term "carrier materials" as used herein refers to materials that are neutral or practically neutral from a fragrance or flavour point of view, that is, the material does not significantly alter the organoleptic properties of perfuming or flavour ingredients.

As carrier materials one can mention, an emulsifying system, i.e. a solvent and a surfactant system, or a solvent commonly used in perfumery or flavours applications. A detailed description of the nature and type of solvents commonly used in perfumery or the flavours industry cannot be exhaustive. However, one can cite as non-limiting examples of solvents useful in perfumery dipropyleneglycol, diethyl phthalate, isopropyl myristate, benzyl benzoate, 2-(2-ethoxyethoxy)-1-ethanol or ethyl citrate.

Carrier materials may also include absorbing gums or polymers, or encapsulating materials. Encapsulation is a well known process to a person skilled in the art, and may be performed, for instance, using techniques such as spray-drying, agglomeration or wet extrusion, or by coacervation or complex coacervation techniques.

The term "perfumery or flavour base" as used herein means a composition comprising at least one perfuming or flavourant co-ingredient that is different from a compound of formula (I).

Moreover, the co-ingredients are used to impart a hedonic effect. For example, such a co-ingredient, if it is to be considered as being a perfuming co-ingredient, must be recognized by a person skilled in the art as being able to impart or modify in a positive or pleasant way the odor of a composition, and not just as having an odor. Similarly, if the co-ingredient is a flavourant it is recognised by a person skilled in the art as being able to create, modify or enhance a flavour accord.

The nature and type of the perfuming or flavourant co-ingredients present in the base do not warrant a more detailed description here, which in any case would not be exhaustive, the skilled person being able to select them on the basis of its general knowledge and according to intended use or application and the desired organoleptic effect.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Specific examples of flavour co-ingredients may include but are not limited to natural flavors, artificial flavors, spices, seasonings, and the like. Exemplary flavoring co-ingredients include synthetic flavor oils and flavoring aromatics and/or oils, oleoresins, essences, distillates, and extracts derived from plants, leaves, flowers, fruits, and so forth, and a combination comprising at least one of the foregoing.

Exemplary flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil; useful flavoring agents include artificial, natural and synthetic fruit flavors such as vanilla, and citrus oils including lemon, orange, lime, grapefruit, yuzu, sudachi, and fruit essences including apple, pear, peach, grape, blueberry, strawberry, raspberry, cherry, plum, prune, raisin, cola, guarana, neroli, pineapple, apricot, banana, melon, apricot, ume, cherry, raspberry, blackberry, tropical fruit, mango, mangosteen, pomegranate, papaya and so forth. Additional exemplary flavors imparted by a flavoring agent include a milk flavor, a butter flavor, a cheese flavor, a cream flavor, and a yogurt flavor; a vanilla flavor; tea or coffee flavors, such as a green tea flavor, an oolong tea flavor, a tea flavor, a cocoa flavor, a chocolate flavor, and a coffee flavor;

mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a chamomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; a nut flavor such as an almond flavor, a hazelnut flavor, a macadamia nut flavor, a peanut flavor, a pecan flavor, a pistachio flavor, and a walnut flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor.

Flavour co-ingredients may include aldehydes and esters such as cinnamyl acetate, cinnamaldehyde, citral diethylacetal, dihydrocarvyl acetate, eugenyl 49 formate, p-methylamisol, and so forth can be used. Further examples of aldehyde flavorings include acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), and the like. Generally any flavoring or food additive such as those described in Chemicals Used in Food Processing, publication 1274, pages 63-258, by the National Academy of Sciences, can be used. This publication is incorporated herein by reference.

The term "adjuvant" as used herein means an ingredient that affects the performance of a composition other than its hedonic performance. For example, an adjuvant may be an ingredient that acts as an aid to processing a composition or article containing a composition, or it may improve handling or storage of said composition or article. It might also be an ingredient that provides additional benefits such as imparting colour or texture to a composition or article. It might also be an ingredient that imparts light resistance or chemical stability to one or more ingredients contained in the composition or article. A detailed description of the nature and type of adjuvant commonly used in perfuming and flavourant compositions cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

Furthermore, the compounds of formula (I) can be used in all the fields of modern perfumery and flavour technology to positively impart or modify the odour of a composition or article into which said compound (I) is added. Consequently, a perfumed or flavoured article comprising at least one compound of formula constitutes another aspect of the present invention.

The nature and type of the constituents of the article do not warrant a more detailed description here, which in any case would not be exhaustive, the skilled person being able to select them on the basis of its general knowledge and according to the nature and the desired effect of said product.

Examples of suitable articles include consumer products that may include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Consumer products may also include any solid or liquid composition that is consumed for at least one of nourishment and pleasure, or intended to be held in the mouth for a period of time before being discarded. A broad general list includes, but is not limited to, foodstuffs of all kinds, confectionery, baked goods, sweet goods, dairy products and beverages, and oral care products.

Some of the above-mentioned consumer product bases may represent an aggressive medium for compounds of the formula (I), so that it may be necessary to protect the latter from premature decomposition, for example by encapsulation.

The proportions in which the compounds of formula (I) can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming or flavourant co-ingredients, solvents or additives commonly used in the art.

For example, in the case of perfuming compositions, typical concentrations are in the order of 0.01% to 3% by weight, or even more, of the compounds of formula (I) based on the weight of the composition into which they are incorporated. Concentrations lower than these, such as in the order of 0.0001% to 0.5% by weight, can be used when these compounds are incorporated into perfumed articles.

In the case of flavourant compositions typical concentrations are in the order of 0.01% to 3% by weight, or even more, of the compounds of formula (I) based on the weight of the composition into which they are incorporated. Concentrations lower than these, such as in the order of 0.0001% to 0.05% by weight, can be used when these compounds are incorporated into flavoured articles.

There now follows a series of examples that serve to illustrate the invention.

EXAMPLE 1

8-sec-Butyl-5,6,7,8-tetrahydroquinoline
(GR-50-0572)

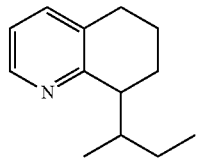

A solution of BuLi (6.8 ml, 1.6 M in hexane) was added dropwise to a cold (−78° C.) solution of 5,6,7,8-tetrahydroquinoline (1.33 g, 10 mmol) in THF (20 ml). The mixture was stirred for 10 min at −78° C. and sec-butyl bromide (1.51 g, 11 mmol) was added dropwise. The mixture was allowed to warm up to room temperature during 1 h, was then carefully quenched with water and extracted with MTBE (3×50 ml). The combined organic phases were washed with water and brine, dried (MgSO4) and concentrated in vacuo. The brown residue was distilled bulb-to-bulb to yield 1.69 g (89%) of the title compound as a colorless oil. This is a general synthetic procedure and the other compounds exemplified were made according to this procedure, duly modified to employ the appropriate alkyl halide alkylating agent in order to add the correct alkyl group at the 8-position.

Odor: green, herbaceous, American ginseng, ginger, tomato leaves, garden peas

2 Isomers in a ratio of 4:6.

$^1$H-NMR (300 MHz, CDCl$_3$): 8.42-8.38 (m, 1H), 7.30-7.27 (m, 1H), 6.98-6.94 (m, 1H), 3.05-2.45 (m, 4H), 2.05-1.85 (m, 2H), 1.68-1.52 (m, 2H), 1.51-1.28 (m, 1H), 1.10-0.097 (m, 4H (isomer A/B)), 0.78 (t, J=7.2 Hz, 3/2H (Isomer A), 0.59 (d, J=206.7 Hz, 3/2H (Isomer B)) ppm. $^{13}$C-NMR (75 MHz, CDCl$_3$): 160.1, 160.0 (s), 146.8, 146.6 (d), 136.2 (d), 133.4, 133.2 (s), 120.3, 120.2 (d), 46.4, 44.3 (d), 37.5, 27.1 (d), 29.7, 29.6, 27.7, 24.6, 23.6, 22.5, 22.0, 21.8 (4t), 17.4, 14.1 (q), 12.5, 12.3 (q) ppm. GC/MS (EI), major-isomer: 189 (M$^+$, 14), 174 (74), 160 (23), 146 (25), 133 (100), 117 (23), 77 (6), 39 (4).

EXAMPLE 2

8-(But-3-en-2-yl)-5,6,7,8-tetrahydroquinoline

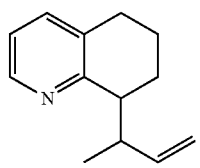

Odor: herbal, metallic, green and ginseng, fruity.

Two isomers in a ratio of 8:2.

$^1$H-NMR (300 MHz, CDCl$_3$): 8.42-8.39 (m, 1H), 7.34-7.28 (m, 1H), 7.02-6.94 (m, 1H), 6.06-5.92 (m, 1H), 5.12-5.00 (m, 2H), 3.50-3.39 (m, 1H), 3.09-2.95 (m, 1H), 2.74-2.64 (m, 2H), 1.97-1.82 (m, 2H), 1.67-1.52 (m, 2H), 0.76 (t, J=6.9 Hz, 3H) ppm. $^{13}$C-NMR (75 MHz, CDCl$_3$) major isomer: 158.9 (s), 146.8 (d), 143.6 (d), 136.4 (d), 133.4 (s), 120.6 (d), 113.1 (t), 45.1 (d), 39.3 (d), 29.6 (t), 23.3 (t), 21.9 (t), 13.0 (q) ppm. GC/MS (EI): 187 (M$^+$, 80), 172 (100), 158 (38), 144 (39), 132 (60), 117 (45), 103 (6), 91 (5), 77 (11), 65 (6), 51 (6), 39 (7).

EXAMPLE 3

8-(But-2-enyl)-5,6,7,8-tetrahydroquinoline

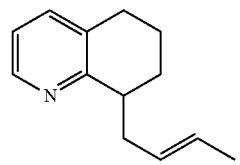

Odor: fruity, earthy, orange flower, green and herbal.

Mixture of (E,Z)-isomers in a ratio of 9:1.

$^1$H-NMR (300 MHz, CDCl$_3$) (E)-isomer: 8.39 (d, J=4.9 Hz, 1H), 7.30 (d, J=7.6 Hz, 1H), 6.98 (dd, J=7.6, 4.9 Hz, 1H), 5.51-5.40 (m, 2H), 2.94-2.81 (m, 1H), 2.79-2.65 (m, 3H), 2.28-2.14 (m, 1H), 1.91-1.56 (m, 7H) ppm. $^{13}$C-NMR (75 MHz, CDCl$_3$): 160.0 (s), 146.8 (d), 136.6 (d), 132.3 (s), 129.8 (d), 126.5 (d), 120.7 (d), 40.7 (d), 38.2 (t), 29.2 (t), 26.9 (t), 19.6 (t), 17.9 (q) ppm. GC/MS (EI): 187 (M$^+$, 44), 172 (100), 158 (43), 144 (54), 132 (92), 117 (67), 103 (8), 91 (6), 77 (19), 65 (8), 51 (8), 39 (11).

EXAMPLE 4

8-(2,3-Dimethylbut-2-enyl)-5,6,7,8-tetrahydroquinoline

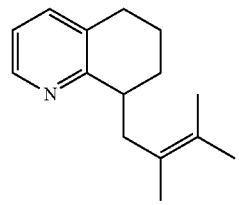 [SMILES: CC(C)=C(C)CC1CCCc2cccnc21]

Odor: green, floral, muguet-like, cologne with petitgrain notes.

$^1$H-NMR (300 MHz, CDCl$_3$): 8.42-8.40 (m, 1H), 7.35-7.32 (m, 1H), 7.03-6.98 (m, 1H), 3.08-2.98 (m, 1H), 2.8-2.71 (m, 2H), 2.65-2.57 (m, 1H), 2.47-2.38 (m, 1H), 1.95-1.61 (m, 4H), 1.74, (s, 3H), 1.69 (s, 3H), 1.68 (s, 3H) ppm. GC/MS (EI): 215 (M$^+$, 38), 200 (38), 172 (39), 133 (100), 117 (25), 103 (4), 77 (7), 55 (10), 41 (9).

EXAMPLE 5

8-Isobutyl-5,6,7,8-tetrahydroquinoline

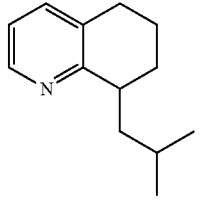

Odor: green, herbaceous, pyrazine, earthy and American ginseng.

$^1$H-NMR (300 MHz, CDCl$_3$): 8.32 (d, J=4.5 Hz, 1H), 6.24 (d, J=7.4 Hz, 1H), 6.92 (dd, J=7.4, 4.5 Hz, 1H), 2.90-2.80 (m, 1H), 2.70-2.62 (m, 2H), 1.92-1.60 (m, 6H), 1.42-1.29 (m, 1H), 0.92 (d, J=6.0 Hz, 3H), 0.87 (d, J=6.0 Hz, 3H) ppm. $^{13}$C-NMR (75 MHz, CDCl$_3$): 160.3 (s), 145.8 (d), 135.6 (d), 131.0 (s), 119.6 (d), 43.3 (t), 37.3 (d), 28.2 (t), 26.1 (t), 24.2 (d), 23.1 (q), 20.1 (q), 18.5 (t) ppm. GC/MS (EI): 189 (M$^+$, 4), 174 (21), 160 (4), 146 (47), 133 (100), 118 (25), 103 (3), 91 (3), 77 (6), 65 (4), 39 (4).

EXAMPLE 6

8-Isopropyl-5,6,7,8-tetrahydroquinoline

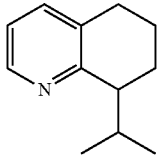

Odor: green, leaf, fresh, camphorated, touch orange blossom and ginseng.

$^1$H-NMR (300 MHz, CDCl$_3$): 8.33 (d, J=4.5 Hz, 1H), 7.23 (d, J=7.5 Hz, 1H), 6.91 (dd, J=7.5, 4.5 Hz, 1H), 2.80-2.62 (m, 4H), 1.89-1.80 (m, 3H), 1.59-1.51 (m, 2H), 0.97 (d, J=6.8 Hz, 3H), 0.58 (d, J=6.8 Hz, 3H) ppm. $^{13}$C-NMR (75 MHz, CDCl$_3$): 159.0 (s), 145.7 (d), 135.4 (d), 132.2 (s), 119.4 (d), 45.1 (d), 29.3 (d), 28.6 (t), 21.8 (t), 20.7 (t), 19.9 (q), 15.9 (q) ppm. GC/MS (EI): 175 (M$^+$, 12), 160 (15), 147 (8), 132 (100), 117 (23), 103 (4), 91 (4), 77 (8), 65 (5), 51 (5), 39 (6).

EXAMPLE 7

8-(Pentan-2-yl)-5,6,7,8-tetrahydroquinoline

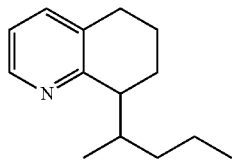

Odor: green, tomato leaf, herbaceous, American ginseng and pyrazine-like

Two Isomers in a ratio of (1:1).

$^1$H-NMR (300 MHz, CDCl$_3$): 8.42-8.39 (m, 1H), 7.32-7.29 (m, 1H), 7.00-6.96 (m, 1H), 2.98-2.84 (m, 1H), 2.78-2.58 (m, 3H), 2.01-1.87 (m, 2H), 1.69-1.53 (m, 2H), 1.48-1.23 (m, 2H), 1.13-0.90 (m, 1H), 1.02, 0.59 (2t, J=7.9 Hz, 3H), 0.95, 0.76 (2t, J=7.0 Hz, 3H) ppm. $^{13}$C-NMR (75 MHz, CDCl$_3$): 160.2, 160.0 (s), 146.8, 146.7 (d), 136.3 (d), 133.4, 133.2 (s), 120.3, 120.2 (d), 46.5, 44.6 (d), 37.5, 34.3 (t), 35.4, 35.1 (d), 29.7 (t), 23.6, 22.6 (t), 22.1, 21.9 (t), 21.0, 20.9 (t), 18.0, 14.3 (q), 14.5 (q) ppm. GC/MS (EI): 203 (M$^+$, 7), 188 (70), 174 (25), 160 (18), 146 (8), 133 (100), 117 (21), 103 (2), 91 (2), 77 (4), 65 (2), 29 (2).

EXAMPLE 8

8-(Pentan-3-yl)-5,6,7,8-tetrahydroquinoline

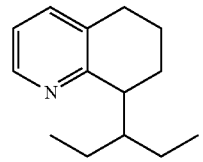

Odor: green, herbal, ginseng and pyrazine-like, fruity, citrus and earthy $^1$H-NMR (300 MHz, CDCl$_3$): 8.41 (d, J=4.1 Hz, 1H), 7.30 (d, J=7.6 Hz, 1H), 6.98 (dd, J=7.6, 4.1 Hz, 1H), 3.11-3.01 (m, 1H), 2.75-2.65 (m, 2H), 2.38-2.28 (m, 1H), 2.00-1.88 (m, 2H), 1.66-1.49 (m, 3H), 1.36-1.21 (m, 1H), 1.13-0.92 (m, 2H), 1.00 (t, J=7.5 Hz, 3H), 0.72 (t, J=7.5 Hz, 3H) ppm. $^{13}$C-NMR (75 MHz, CDCl$_3$): 160.6 (s), 146.7 (d), 136.2 (d), 133.5 (s), 120.2 (d), 44.2 (d), 42.5 (d), 29.8 (t), 24.2 (t), 23.4 (t), 23.3 (t), 22.1 (t), 12.8 (q), 12.3 (q) ppm. GC/MS (EI): 203 (M$^+$, 7), 188 (72), 174 (22), 160 (20), 146 (9), 133 (100), 117 (25), 103 (2), 77 (5), 65 (3), 39 (3).

EXAMPLE 9

8-Cyclohexyl-5,6,7,8-tetrahydroquinoline

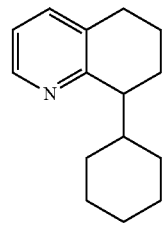 [SMILES: c1cnc2c(c1)CCCC2C1CCCCC1]

Odor: green, herbaceous, green bean-like, oranger flower, petitgrain $^1$H-NMR (300 MHz, CDCl$_3$): 8.41 (d, J=4.7 Hz, 1H), 7.31 (d, J=7.5 Hz, 1H), 6.98 (dd, J=7.5, 4.7 Hz, 1H), 2.86-2.80 (m, 1H), 2.73-2.65 (m, 2H), 2.39-2.30 (m, 1H), 1.95-1.87 (m, 2H), 1.78-1.59 (m, 6H), 1.44-0.96 (m, 6H) ppm. $^{13}$C-NMR (75 MHz, CDCl$_3$): 159.9 (s), 146.7 (d), 136.3 (d), 133.2 (s), 120.3 (d), 45.9 (d), 41.4 (d), 31.6 (t), 29.5 (t), 27.7 (t), 27.0 (t), 26.8 (t), 26.7 (t), 24.1 (t), 21.6 (t) ppm. GC/MS (EI): 215 (M+, 8), 187 (6), 172 (11), 158 (5), 144 (6), 133 (100), 117 (12), 77 (4), 55 (4), 41 (4).

EXAMPLE 10

8-(2-Methallyl)-5,6,7,8-tetrahydroquinoline

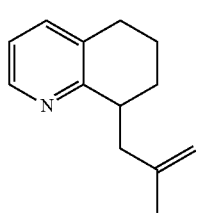

Odor: fruity, earthy, oranger flower, green and herbal

¹H-NMR (300 MHz, CDCl₃): 8.40 (d, J=4.7 Hz, 1H), 7.33 (d, J=7.5 Hz, 1H), 7.00 (dd, J=7.5, 4.7 Hz, 1H), 4.81 (s, 1H), 4.73 (s, 1H), 3.09-3.01 (m, 1H), 2.84 (bdd, J=13.6, 3.6 Hz, 1H), 2.68-2.72 (m, 2H), 2.18 (dd, J=13.6, 11.5 Hz, 1H), 1.90-1.66 (m, 4H), 1.80 (s, 3H) ppm. ¹³C-NMR (75 MHz, CDCl₃): 160.2 (s), 146.9 (d), 144.4 (s), 136.6 (d), 132.2 (s), 120.8 (d), 112.1 (t), 43.6 (t), 38.1 (d), 29.2 (t), 26.3 (t), 21.7 (q), 19.2 (t) ppm. GC/MS (EI): 187 (M+, 83), 186 (100), 172 (81), 159 (46), 144 (45), 130 (59), 117 (58), 103 (8), 91 (7), 77 (17), 65 (10), 51 (8), 39 (12).

EXAMPLE 11

8-Hexyl-5,6,7,8-tetrahydroquinoline

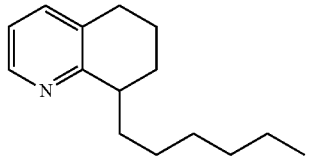 [SMILES: CCCCCCC1CCCc2cccnc21]

Odor: green, leafy, fruity and petitgrain-like, powerful.

¹H-NMR (300 MHz, CDCl₃): 8.39 (d, J=4.7 Hz, 1H), 7.31 (d, J=7.5 Hz, 1H), 6.98 (dd, J=7.5, 4.7 Hz, 1H), 2.89-2.78 (m, 1H), 2.77-2.69 (m, 2H), 2.05-1.25 (m, 14H), 0.88 (t, J=6.8 Hz, 3H) ppm. ¹³C-NMR (75 MHz, CDCl₃): 160.9 (s), 146.8 (d), 136.5 (d), 132.0 (s), 120.6 (d), 40.7 (d), 35.3 (t), 31.9 (t), 29.5 (t), 29.2 (t), 27.4 (t), 27.3 (t), 22.6 (t), 19.7 (t), 14.0 (q) ppm. GC/MS (EI): 217 (M+, 9), 188 (2), 160 (13), 146 (32), 133 (100), 118 (13), 103 (1), 77 (2), 39 (1).

EXAMPLE 12

7-sec-Butyl-6,7-dihydro-5H-cyclopenta[b]pyridine

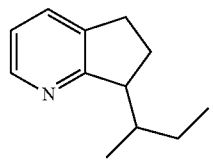

Odor: green, leafy with pea note, fruity, slightly camphoraceous.

2 Isomers in a ratio of 1:1)

¹H-NMR (300 MHz, CDCl₃): 8.31 (bs, 1H), 7.40-7.37 (m, 1H), 6.95-6.91 (m, 1H), 3.26-3.09 (m, 1H), 2.87-2.74 (m, 2H), 2.19-1.75 (m, 3H), 1.47-0.98 (m, 2H), 0.90, 0.59 (2d, J=6.8 Hz, 3H), 0.92, 0.78 (2t, J=7.4 Hz, 3H) ppm. GC/MS (EI): 175 (M+, 2), 160 (4), 146 (13), 130 (7), 119 (100), 91 (10), 77 (3), 65 (5), 39 (5).

EXAMPLE 13

7-(Pentan-2-yl)-6,7-dihydro-5H-cyclopenta[b]pyridine

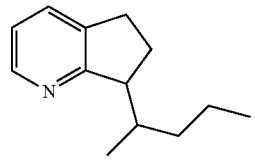

Odor: green, herbaceous, aromatic, floral (lily of the valley), less ginseng and pyrazine-like.

Mixture of 2 isomers in a ratio of 1:1).

¹H-NMR (300 MHz, CDCl₃): 8.38 (bs), 7.47-7.45 (m, 1H), 7.03-6.99 (m, 1H), 3.31-3.24, 3.21-3.14 (2m, 1H), 2.95-2.76 (m, 2H), 2.40-1.83 (m, 3H), 1.48-1.07 (m, 4H), 1.00, 0.65 (2d, J=7.0 Hz, 3H), 0.94, 0.82 (2t, J=7.0 Hz, 3H) ppm. ¹³C-NMR (75 MHz, CDCl₃): 167.2, 167.0 (s), 147.5, 147.4 (d), 137.5, 137.4 (s), 1.31.8, 131.7 (d), 120.8 (d), 51.2, 49.6 (d), 37.9, 34.4 (t), 35.5, 34.4 (d), 29.4 (t), 25.1, 23.3 (t), 20.7, 20.6 (t), 17.8, 14.3 (q), 14.3 (q) ppm. GC/MS (EI): 189 (M⁺, 5), 174 (5), 160 (3), 146 (26), 119 (100), 91 (9), 77 (2), 65 (3), 39 (3).

EXAMPLE 14

7-(Pentan-3-yl)-6,7-dihydro-5H-cyclopenta[b]pyridine

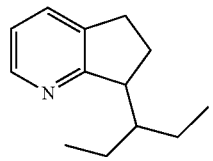

Odor: green, tomato leaf, aromatic, herbaceous, floral (lily of the valley), less ginseng and pyrazine-like.

$^1$H-NMR (300 MHz, CDCl$_3$): 8.38 (d, J=4.9 Hz, 1H), 7.44 (d, J=7.1 Hz, 1H), 6.99 (dd, J=7.1, 4.9 Hz, 1H), 3.42-3.36 (m, 1H), 2.94-2.76 (m, 2H), 2.17-2.05 (m, 1H), 1.99-1.81 (m, 2H), 1.68-1.54 (m, 1H), 1.37-1.23 (m, 1H), 1.15-1.06 (m, 2H), 1.00 (t, J=7.5 Hz, 3H), 0.81 (t, J=7.5 Hz, 3H) ppm. $^{13}$C-NMR (75 MHz, CDCl$_3$): 167.6 (s), 147.5 (d), 137.5 (s), 131.7 (d), 120.8 (d), 47.5 (d), 43.7 (d), 29.4 (t), 24.5 (t), 24.1 (t), 22.6 (t), 12.4 (q), 12.1 (q) ppm. GC/MS (EI): 189 (M⁺, 2), 160 (23), 132 (4), 119 (100), 91 (4), 77 (1), 65 (2), 39 (2).

EXAMPLE 15

7-(2-Methallyl)-6,7-dihydro-5H-cyclopenta[b]pyridine

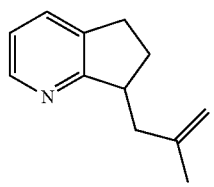

Odor: green, orange flower (neroli), pungent.

$^1$H-NMR (300 MHz, CDCl$_3$): 8.37 (d, J=4.9 Hz, 1H), 7.47 (d, J=7.9 Hz, 1H), 7.02 (dd, J=7.9, 4.9 Hz, 1H), 4.80 (s, 1H), 4.76 (s, 1H), 3.38-3.28 (m, 1H), 2.95-2.77 (m, 3H), 2.32-2.21 (m, 1H), 2.05 (dd, J=14.0, 11.2 Hz, 1H), 1.83-1.71 (m, 1H), 1.80 (s, 3H) ppm. $^{13}$C-NMR (75 MHz, CDCl$_3$): 167.4 (s), 147.52 (d), 144.4 (s), 136.7 (s), 132.1 (d), 121.2 (d), 111.4 (t), 43.5 (d), 42.2 (t), 29.3 (t), 28.8 (t), 22.4 (q) ppm. GC/MS (EI): 173 (M⁺, 62), 172 (77), 158 (50), 144 (10), 132 (32), 118 (100), 91 (25), 77 (7), 65 (9), 51 (5), 39 (10).

EXAMPLE 16

7-Isobutyl-6,7-dihydro-5H-cyclopenta[b]pyridine

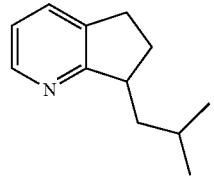

Odor: green, earthy, ginseng.

$^1$H-NMR (300 MHz, CDCl$_3$): 8.36 (d, J=4.9 Hz, 1H), 7.47 (d, J=7.3 Hz, 1H), 7.01 (dd, J=4.9, 7.3 Hz, 1H), 3.23-3.13 (m, 1H), 2.96-2.77 (m, 2H), 2.40-2.29 (m, 1H), 1.98-1.64 (m, 3H), 1.38-1.29 (m, 1H), 0.9 (d, J=6.4 Hz, 3H), 0.8 (d, J=6.4 Hz, 3H) ppm. GC/MS (EI): 175 (M⁺, 4), 160 (7), 132 (61), 118 (110), 107 (3), 91 (10), 77 (5), 65 (5), 39 (6).

EXAMPLE 17

7-(3-Methylbut-2-enyl)-6,7-dihydro-5H-cyclopenta[b]pyridine

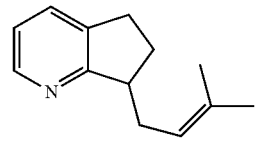

Odor: green, leafy, floral, orange flower, petitgrain.

$^1$H-NMR (300 MHz, CDCl$_3$): 8.37 (d, J=4.9 Hz, 1H), 7.47 (d, J=7.4 Hz, 1H), 7.02 (dd, J=7.4, 4.9 Hz, 1H), 5.22-5.17 (m, 1H), 3.22-3.12 (m, 1H), 3.03-2.66 (m, 3H), 3.32-2.09 (m, 2H), 1.82-1.69 (m, 1H), 1.70 (s, 3H), 1.62 (s, 3H) ppm. GC/MS (EI): 187 (M⁺, 18), 172 (37), 144 (7), 130 (8), 118 (100), 91 (12), 69 (6), 41 (11).

EXAMPLE 18

7-(But-3-ene-2-yl)-6,7-dihydro-5H-cyclopenta[b]pyridine

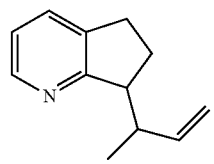

Odor: green, herbal, fruity, ginseng and pyrazine-like.
Two Isomers in a ratio of 2:8.

$^1$H-NMR (300 MHz, CDCl$_3$) major isomer: 8.39 (d, J=4.2 Hz, 1H), 7.47 (d, J=7.4 Hz, 1H), 7.02 (dd, J=7.4, 4.2 Hz, 1H), 5.92 (ddd, J=17.4, 10.4, 6.6 Hz, 1H), 5.08 (d, J=17.4 Hz, 1H), 5.02 (d, J=10.4 Hz, 1H), 3.36-3.30 (m, 1H), 3.04-2.79 (m, 3H), 2.19-2.06 (m, 1H), 1.97-1.85 (m, 1H), 0.86 (d, J=6.8 Hz, 3H) ppm. $^{13}$C-NMR (75 MHz, CDCl$_3$): 166.2 (s), 147.6 (d), 143.0 (d), 137.6 (s), 132.0 (d), 113.2 (t), 49.8 (d), 39.6 (d), 29.4 (t), 24.3 (t), 13.9 (q) ppm. GC/MS (EI): 173 (M$^+$, 24), 172 (24), 158 (53), 118 (100), 91 (20), 77 (5), 65 (7), 51 (4), 39 (7).

EXAMPLE 19

7-Pentyl-6,7-dihydro-5H-cyclopenta[b]pyridine

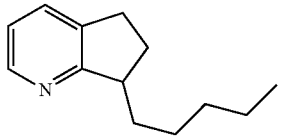

Odor: green, floral, pyrazine, hyacinth-like, powerful.

$^1$H-NMR (300 MHz, CDCl$_3$): 8.36 (d, J=4.5 Hz, 1H), 7.47 (d, J=7.3 Hz, 1H), 7.01 (dd, J=&.3, 4.5 Hz, 1H), 3.15-3.05 (m, 1H), 2.96-2.77 (m, 2H), 2.39-2.27 (m, 1H), 2.14-1.98 (m, 1H), 1.79-1.67 (m, 1H), 1.50-1.29 (m, 7H), 0.89 (t, J=6.9 Hz, 3H) ppm. $^{13}$C-NMR (75 MHz, CDCl$_3$): 168.0 (s), 147.4 (d), 136.8 (s), 132.0 (d), 121.0 (d), 45.5 (d), 33.8 (t), 32.0 (t), 30.0 (t), 29.1 (t), 27.2 (t), 22.6 (t), 14.1 (q) ppm. GC/MS (EI): 189 (M$^+$, 7), 132 (45), 119 (100), 91 (8), 77 (3), 65 (3), 39 (3).

EXAMPLE 20

7-Cyclohexyl-6,7-dihydro-5H-cyclopenta[b]pyridine

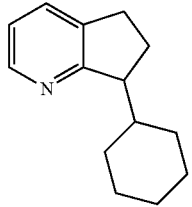 [SMILES: c1cnc2c(c1)CCC2C1CCCCC1]

Odor: green, herbaceous, green bean, petitgrain-like.

$^1$H-NMR (300 MHz, CDCl$_3$): 8.28 (d, J=4.9 Hz, 1H), 7.34 (d, J=7.5 Hz, 1H), 6.89 (dd, J=7.5, 4.9 Hz, 1H), 3.03-2.97 (m, 1H), 2.83-2.65 (m, 2H), 2.09-1.79 (m, 3H), 1.73-1.55 (m, 4H), 1.30-0.91 (m, 6H) ppm. $^{13}$C-NMR (75 MHz, CDCl$_3$): 166.9 (s), 147.4 (d), 137.3 (s), 131.7 (d), 120.8 (d), 50-0.9 (d), 40.8 (d), 31.7 (t), 29.5 (t), 27.9 (t), 26.7 (t), 26.6 (t), 26.4 (t), 25.1 (t) ppm. GC/MS (EI): 200 (M$^{-1}$, 1), 158 (3), 130 (3), 119 (100), 91 (6), 77 (2), 55 (4), 41 (4).

EXAMPLE 21

An organic spicy, ginger perfume application in which 8-sec-butyl-5,6,7,8-tetrahydroquinoline enhances the citrus character, gives freshness and creates a natural green aspect.

| | |
|---|---|
| Benzyl acetate | 25.00 |
| Bornyl acetate | 8.00 |
| Phenyl ethyl acetate | 2.00 |
| Phenoxy ethyl alcohol | 45.00 |
| Phenylethyl alcohol | 82.00 |
| Cyclamen aldehyde | 20.00 |
| Ambrofix | 3.00 |
| Bergamote ess. | 200.00 |
| Bergamote ess. Italie | 100.00 |
| Citral lemarome | 5.00 |
| Citron ess. Italie Orpur | 100.00 |
| Citronellol extra | 52.00 |
| Cosmone | 4.00 |
| Coumarine | 15.50 |
| gamma-Decalactone | 5.00 |
| Dipropylene glycol | 27.00 |
| Ethyl linalool | 50.00 |
| Eucalyptol | 2.00 |
| Eugenol pure | 5.00 |
| Galaxolide | 100.00 |
| Ginger purple extract Orpur | 70.00 |
| Ginger root fresh cut | 1.50 |
| Hedione | 200.00 |
| Heliotropine | 5.00 |
| Isorealdeine 70 | 20.00 |
| cis-Jasmone | 1.00 |
| Miel Blanc2/20 | 4.00 |
| Opalal | 50.00 |
| Orange ess Brasil | 20.00 |
| Peche pure at 10% in DPG | 5.00 |
| Rajanol super | 8.00 |
| Terpineol pure | 10.00 |
| 8-sec-butyl-5,6,7,8-tetrahydroquinoline | 5.00 |
| Total | 1250.00 |

The invention claimed is:

1. A fragrance or flavour composition or a flavoured article or a perfumed article comprising a compound of formula (I)

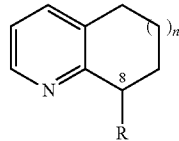

Formula (I)

wherein:

n=0, 1, 2, or 3 and

R is a $C_2$-$C_6$ alkyl, alkenyl or cycloalkyl substituent which may be linear or branched.

2. A method to confer, enhance, improve or modify the hedonic properties of a perfuming composition or of a perfumed article, or of a flavour composition or flavoured article, which method comprises adding to said composition or article a compound of formula (I)

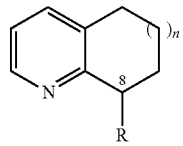

Formula (I)

wherein:

n=0, 1, 2, or 3 and

R is a $C_2$-$C_6$ alkyl, alkenyl or cycloalkyl substituent which may be linear or branched.

3. A compound having flavouring or fragrance characteristic according to formula (I)

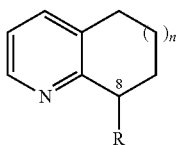

Formula (I)

wherein:
n=0, 1, 2, or 3 and
R is a $C_2$-$C_6$ alkyl, alkenyl or cycloalkyl substituent which may be linear or branched with the proviso that said compound is not a compound selected from the group consisting of:

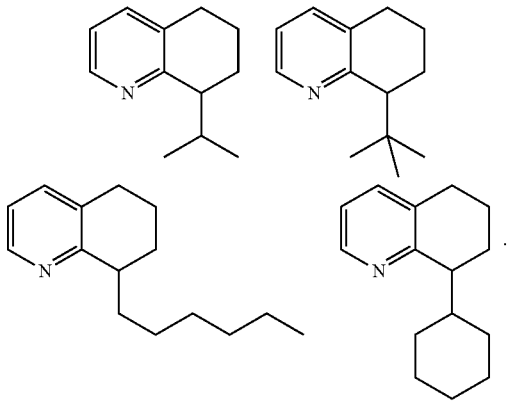

4. A compound according to claim 3 selected from the group consisting of:
8-sec-Butyl-5,6,7,8-tetrahydroquinoline
8-(Pentan-2-yl)-5,6,7,8-tetrahydroquinoline
8-(Pentan-3-yl)-5,6,7,8-tetrahydroquinoline
7-sec-Butyl-6,7-dihydro-5H-cyclopenta[b]pyridine
7-(Pentan-2-yl)-6,7-dihydro-5H-cyclopenta[b]pyridine
7-(Pentan-3-yl)-6,7-dihydro-5H-cyclopenta[b]pyridine
7-(3-Methylbut-2-enyl)-6,7-dihydro-5H-cyclopenta[b]pyridine.

5. A method of providing a flavoring or fragance characteristic to a consumer article or consumer product the method comprising the step of:
including in the composition of the consumer article or consumer product a compound having flavoring or fragrance characteristics of formula (I)

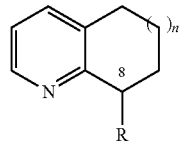

Formula (I)

wherein:
n=0, 1, 2, or 3 and
R is a $C_2$-$C_6$ alkyl, alkenyl or cycloalkyl substituent, which may be linear or branched, which is effective to enhance, improve or modify the hedonic properties of a perfuming composition or of a perfumed article, or of a flavour composition or flavoured article.

6. A method according to claim 5, wherein the consumer product is selected from:
solid or liquid detergents, fabric softeners, perfumes, colognes or after-shave lotions, perfumed soaps, shower or bath salts, mousses, oils, gels, hygiene products, hair care products, shampoos, body-care products, deodorants, antiperspirants, air fresheners, cosmetic preparations, detergent compositions or cleaning products for washing up or for cleaning various surfaces, e.g. intended for textile, dish or hard-surface treatment, fabric refreshers, ironing waters, papers, wipes or bleaches.

7. A method according to claim 5, wherein the consumer product is selected from: any solid or liquid composition that is consumed for at least one of nourishment and pleasure, or intended to be held in the mouth for a period of time before being discarded, foodstuffs, confectionery, baked goods, sweet goods, dairy products and beverages, and oral care products.

* * * * *